United States Patent [19]
Brichard et al.

[11] Patent Number: 5,856,091
[45] Date of Patent: Jan. 5, 1999

[54] ISOLATED NUCLEIC ACID SEQUENCE CODING FOR A TUMOR REJECTION ANTIGEN PRECURSOR PROCESSED TO AT LEAST ONE TUMOR REJECTION ANTIGEN PRESENTED BY HLA-A2

[75] Inventors: Vincent Brichard; Aline Van Pel, both of Brussels, Belgium; Catia Traversari, Milan, Italy; Thomas Wölfel, Mainz, Germany; Pierre Coulie, Brussels, Belgium; Thierry Boon-Falleur, Brussels, Belgium; Etienne De Plaen, Brussels, Belgium

[73] Assignee: Ludwig Institute for Cancer Research, New York, N.Y.

[21] Appl. No.: 370,319

[22] Filed: Jan. 10, 1995

Related U.S. Application Data

[63] Continuation-in-part of Ser. No. 272,351, Jul. 8, 1994, abandoned, which is a continuation-in-part of Ser. No. 32,978, Mar. 18, 1993, Pat. No. 5,620,886.

[51] Int. Cl.$^6$ .................................................. C12N 15/11
[52] U.S. Cl. ...................... 435/6; 435/252.3; 435/320.1; 435/325; 536/23.1; 536/24.31; 536/24.33
[58] Field of Search ............................... 435/325, 172.1, 435/320.1, 252.3, 6; 530/350; 536/23.1, 24.31, 24.33

[56] References Cited

U.S. PATENT DOCUMENTS 5,487,974   1/1996   Boon-Falleur et al. ..................... 435/6

OTHER PUBLICATIONS

Kawakami et al., "Cloning of the Gene Coding For a Shared Human Melanoma Antigen Recognized By Autologous T Cells Infiltrating Into Tumor", Proc. Natl. Acad. Sci. USA 91: 3515–3519 (Apr. 1994).

Traversari et al., "A Nonapeptide Encoded by Human Gene MAGE–1–Is Recognized on HLA–A1 by Cytolytic T Lymphocytes Directed Against Tumor Antigen MZ2–E", J. Exp. Med. 176: 1453–1457 (Nov. 1992).

Van der Bruggen et al., "A Gene Encoding an Antigen Recognized–by Cytolytic T Lymphocytes on a Human Melanoma", Science 254: 1643–1647 (Dec. 13, 1991).

Van den Eynde et al., "Presence on a Human Melanoma of Multiple–Antigens Recognized by Autologous CTL", Int. J. Cancer 44: 634–640 (1989).

Bodmer et al., "Anti–HLA–A2 antibody–enhancement of peptide–association with HLA–A2 as detected by cytotoxic T lymphocytes", Nature 342: 443–446 (Nov. 23, 1989).

Wölfel et al., "Lysis of Human Melanoma Cells by Autologous–Cytolytic T Cell Clones", J. Exp. med. 170: 797–810 (Sep. 1989).

Knuth et al., "Cytolytic T–cell clones against an autologous–human melanoma: specificity study and definition of three antigens by immunoselection", Proc. Natl. Acad. Sci. USA 86: 2804–2808 (Apr. 1989).

Kwon et al (1987) PNAS 84:7473–7477 "Isolation and sequence of a cDNA clone for human tyrosinase that maps at the mouse c–albino locus".

Giebel et al. (1991) Genomics 9:435–445 "Organization and Nucleotide sequences of the human tyrosinase gene and a truncated tyrosine–related segment".

Primary Examiner—Charles L. Patterson, Jr.
Attorney, Agent, or Firm—Fulbright & Jaworski, LLP

[57] ABSTRACT

The invention relates to nucleic acid molecules coding for a tumor rejection antigen precursor. Specifically, the tumor rejection antigen precursor, or "TRAP", is processed into at least one tumor rejection antigen, which is presented by HLA-A2 molecules. Ramifications of the discovery are also set forth.

21 Claims, 6 Drawing Sheets

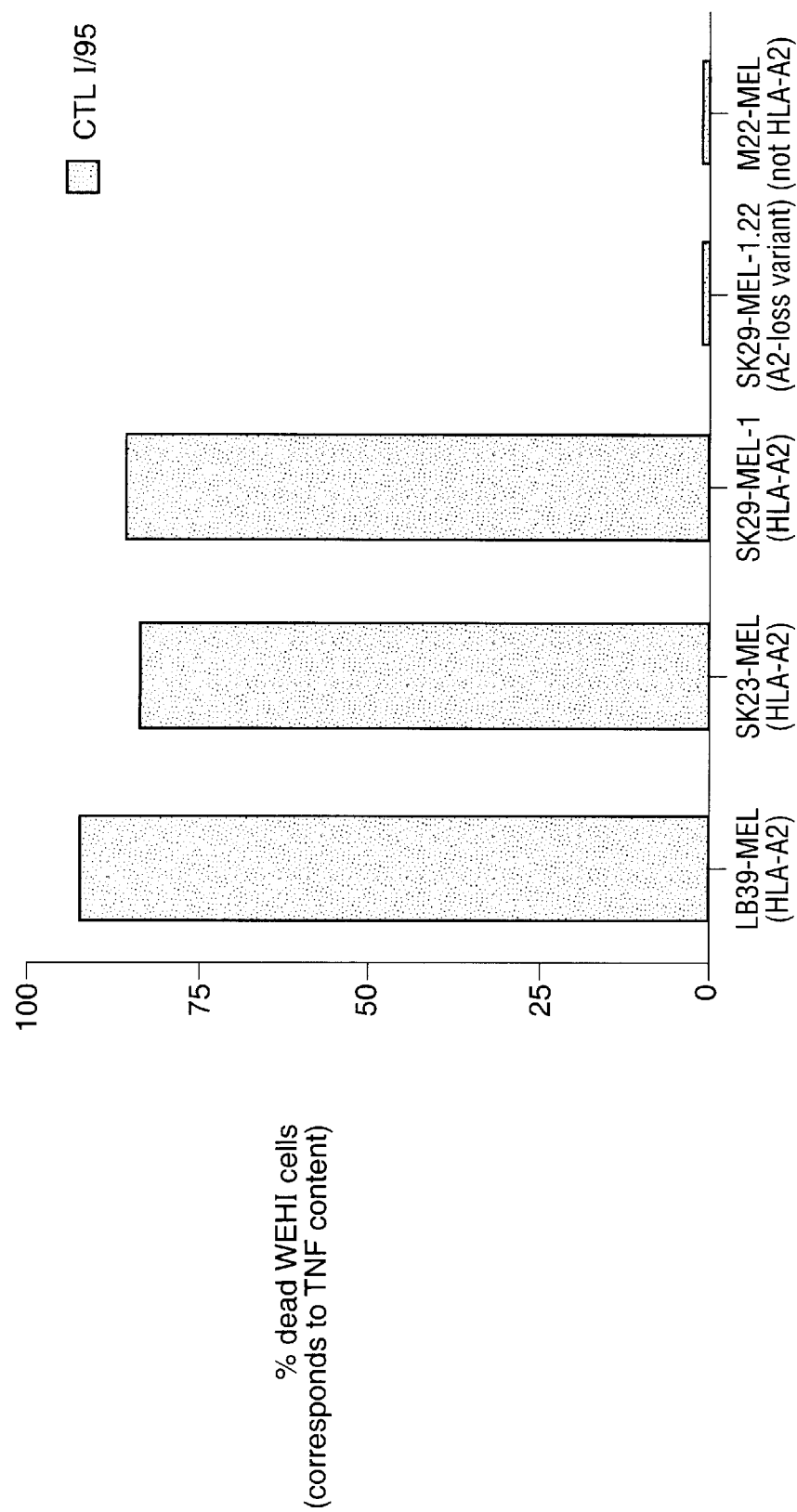

FIG. 4

| NORMAL TISSUES | As |
|---|---|
| melanocytes SK | + |
| heart | − |
| liver | − |
| kidney BA4 | − |
| prostate Clontech | − |
| adrenals | − |
| adrenals | − |
| adrenals | − |
| adrenals pool Clontech | − |
| testis Clontech | − |
| testis LB451 | − |
| brain Clontech | − |
| fetal brain Clontech | − |
| lung LB175 | − |
| lung LB195 | − |
| skin LB 177 | − |
| CTL SK29 IVS B | − |

MELANOMA

| CELL LINES | | TUMOR SAMPLES | |
|---|---|---|---|
| LB24-MEL | + | LB239-MEL | + |
| SK23-MEL | + | LB15-MEL | + |
| LE518-MEL | + | LB492-MEL | + |
| LB38-MEL | + | LB503-MEL | + |
| MZ13-MEL | − | LB435-MEL | + |
| LB33-MEL | − | LB224-MEL | + |
| LB3-MEL | + | LG18-MEL | + |

| OTHER TUMOR CELL LINES | |
|---|---|
| LB23 sarcoma | − |
| LE89.15 kidney tumor | − |
| BT20 breast caroinoma | − |
| LB63 colon carcinoma | − |
| T cell leukemia | − |

ISOLATED NUCLEIC ACID SEQUENCE CODING FOR A TUMOR REJECTION ANTIGEN PRECURSOR PROCESSED TO AT LEAST ONE TUMOR REJECTION ANTIGEN PRESENTED BY HLA-A2

RELATED APPLICATIONS

This application is a continuation-in-part of Ser. No. 08/272,351, filed Jul. 8, 1994, now abandoned which is a continuation-in-part of patent application Ser. No. 08/032, 978 filed Mar. 18, 1993, now U.S. Pat. No. 5,620,886.

FIELD OF THE INVENTION

This invention relates to a nucleic acid molecule which codes for a tumor rejection antigen precursor. More particularly, the invention concerns a gene, whose tumor rejection antigen precursor is processed, inter alia, into at least one tumor rejection antigen that is presented by HLA-A2 molecules on cell surfaces.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also see U.S. Pat. No. 5,342,774, incorporated by reference.

In U.S. patent application Ser. No. 938,334, now U.S. Pat. No. 5,405,940 the disclosure of which is incorporated by reference, nonapeptides are taught which are presented by the HLA-A1 molecule. The reference teaches that, given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-C*1601-molecules. The disclosure shows that a given TRAP can yield a plurality of TRAs.

In U.S. patent application Ser. No. 994,928, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

U.S. patent application Ser. No. 32,978 cited supra, reports on a nucleic acid molecule which codes for a tumor rejection antigen precursor which differs from those described previously. The TRAP of the invention described therein is processed to at least one tumor rejection antigen that is presented by HLA-A2 molecules; however sequence analysis indicated that the TRAP of the invention is not, nor is it related to, tyrosinase. Thus the invention of the parent application relates to a nucleic acid molecule which codes for a tumor rejection antigen precursor, or "TRAP" molecule. This "TRAP" molecule is not tyrosinase. Further, the TRAP of the invention of the parent application is processed to at least one tumor rejection antigen, or "TRA", which is presented by HLA-A2 molecules. The TRA is not tyrosinase related, and other TRAs derived from the TRAPs of the invention may be presented by other HLA molecules.

In a paper published after the above-identified parent application, Kawakami, et al., Proc. Natl. Acad. Sci. USA 91: 3513–3519 (1994) also identified the subject matter of the parent application as a gene coding for a melanoma antigen.

Further work shows that the gene coding for this TRAP, referred to as hereafter as "Melan-A", is about 18 kilobases long, and comprises 5 exons. It appears to be expressed only in melanoma and melanocytes, thus serving as a marker for these cells.

The invention and various aspects thereof will be elaborated upon in the disclosure which follows.

BRIEF DESCRIPTION OF THE FIGURES

FIG. 2 sets forth results of a TNF release assay using various cell lines with CTL I/95.

FIG. 4 presents a panel of tissues, cell lines and tumors tested for expression of the Melan A gene, "AaG1cl24" via polymerase chain reaction (PCR) using oligonucleotide probes derived from the nucleic acid molecule described herein.

DETAILED DESCRIPTION OF PREFERRED EMBODIMENTS

EXAMPLE 1

A melanoma cell line, "LB-39-MEL" was established from melanoma cells taken from patient LB39, using standard methodologies. Once the cell line was established, a sample thereof was irradiated, so as to render it nonproliferative. These irradiated cells were then used to isolate cytolytic T cells ("CTLs") specific thereto.

A sample of peripheral blood mononuclear cells ("PBMCs") was taken from patient LB39, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in an 80% CO$_2$ atmosphere.

Plates were centrifuged again, and 100 ul aliquots of supernatant were collected and counted. Percentage of $^{51}$Cr release was calculated as follows:

$$\% \; ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology. The CTL clone LB39-CTL I/95 was thus isolated.

Figure 1C:
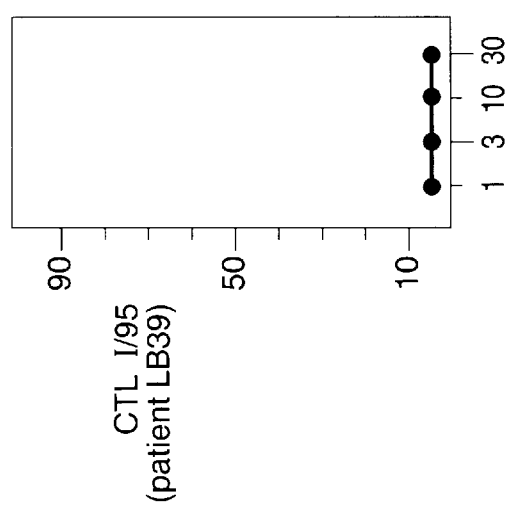
FIGS. 1A–1C present results of cell lysis experiments using CTL clone I/95 against LB39-MEL, K562, and LB39 blasts.
Figure 1B:
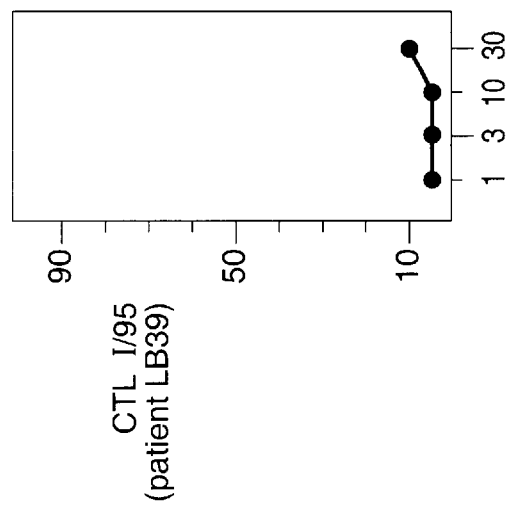
Figure 1A:
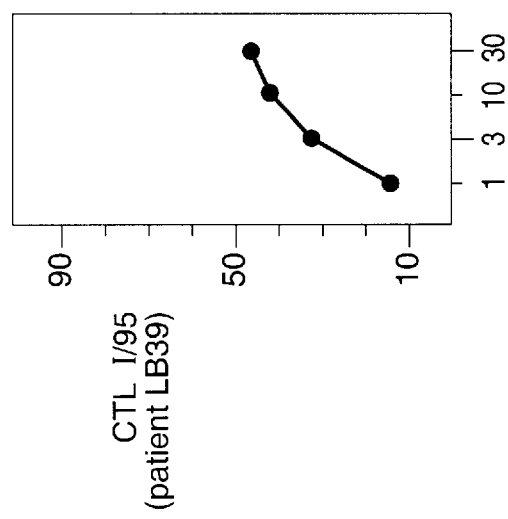
Figure 1D:
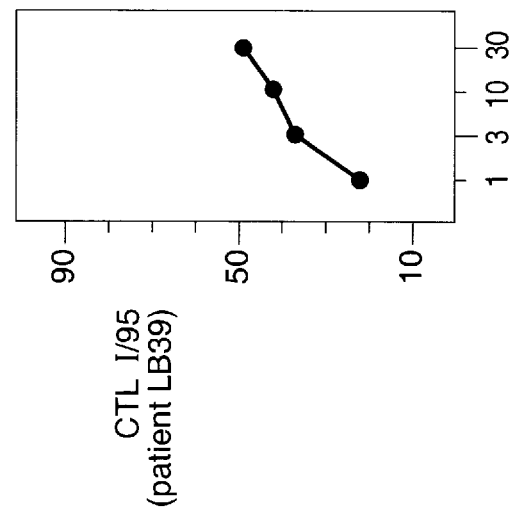
FIGS. 1D–1E show lysis using CTL clone I/95 against SK23-MEL and SK29-MEL.
Figure 1E:
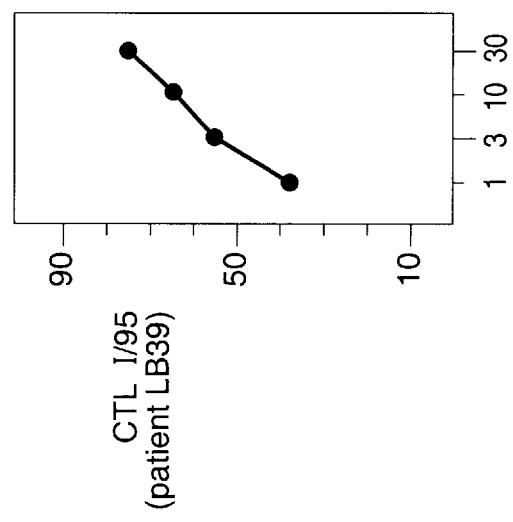

The same method was used to test target K562 cells, as well as autologous, PHA induced T cell blasts. These results, presented in FIG. 1A, show that this CTL clone recognizes and lyses the melanoma cell line, but neither of K562 or the T cell blasts. The CTL, LB39-CTL I/95, was then tested against melanoma cell lines SK23-MEL and SK29 MEL, in the same manner described supra. Cells from both of these lines were also lysed. These lines were both isolated from patients who were typed as HLA-A2, as was LB39. This suggested that the CTL clone LB39-CTL I/95 recognized an antigen presented by HLA-A2.

EXAMPLE 2

Further studies were carried out to determine if LB39-CTL I/95 also produced tumor necrosis factor ("TNF") when contacted with target cells. The method used was that described by Traversari et al., Immunogenetics 35: 145–152 (1992), the disclosure of which is incorporated by reference. Briefly, samples of the CTL line were combined with samples of a target cell of interest, in culture medium. After 24 hours, supernatant from the cultures was removed, and then tested on TNF sensitive WEHI cells. In addition to LB39-MEL and SK23-MEL, described supra, another HLA-A2 line, i.e., SK29-MEL.1, an HLA-A2 loss variant, i.e., SK29-MEL.1.22, and a non HLA-A2 line, i.e., MZ2-MEL, which is HLA-A1 positive, were tested.

The results, presented in terms of the percentage of WEHI cells which died upon exposure to the supernatant, are shown in FIG. 2. These results show that the HLA-A2 loss variant SK 29-MEL.1.22 is no longer capable of stimulating the CTL clone, thus confirming that the antigen recognized by LB39-CTL-I/95 is presented by HLA-A2.

EXAMPLE 3

The results from Example 2 indicated that SK29-MEL.1 presented the target antigen of interest. As such, it was used as a source of total mRNA to prepare a cDNA library.

Total RNA was isolated from the cell line. The mRNA was isolated using an oligo-dT binding kit, following well recognized techniques. Once the mRNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into JM101 E. coli (electroporation conditions: 1 pulse at 25 $\mu$farads, 2500 V).

The transfected bacteria were selected with ampicillin (50 $\mu$g/ml), and then divided into 800 pools of 100 clones each. Each pool represented about 50 different cDNAs, as analysis showed that about 50% of plasmids contained an insert. Each pool was amplified to saturation, and plasmid DNA was isolated via alkaline lysis, potassium acetate precipitation without phenol extraction, following Maniatis et al., in Molecular Cloning: A Laboratory Manual (Cold Spring Harbor, N.Y., 1982).

EXAMPLE 4

Following preparation of the library described in Example 3, the cDNA was transfected into eukaryotic cells. The transfections, described herein, were carried out in duplicate. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 $\mu$l/well of DMEM medium containing 10% Nu serum, 400 $\mu$g/ml DEAE-dextran, 100 $\mu$M chloroquine, 100 ng of plasmid pcDNA-I/Amp-A2 and 100 ng of DNA of a pool of the cDNA library described supra. Plasmid pcDNA-I/Amp-A2 contains the HLA-A2 gene from SK29-MEL.1. Following four hours of incubation at 37° C., the medium was removed, and replaced by 50 $\mu$l of PBS containing 10%

DMSO. This medium was removed after two minutes and replaced by 200 µl of DMEM supplemented with 10% of FCS.

Following this change in medium, COS cells were incubated for 48 hours at 37° C. Medium was then discarded, and 1000 cells of CTL I/95 were added, in 100 µl of Iscove's medium containing 10% pooled human serum, supplemented with 25 U/ml of IL-2. Supernatant was removed after 24 hours, and TNF content was determined in the assay on WEHI cells, as described by Traversari et al., supra, previously incorporated by reference.

Of the 800 pools tested, 99% stimulated TNF release, to a concentration of from 3–6 pg/ml in the supernatant. Two pools gave yields over 8 pg/ml, with a duplicate well also yielding over 8 pg/ml.

EXAMPLE 5

Figure 3A:
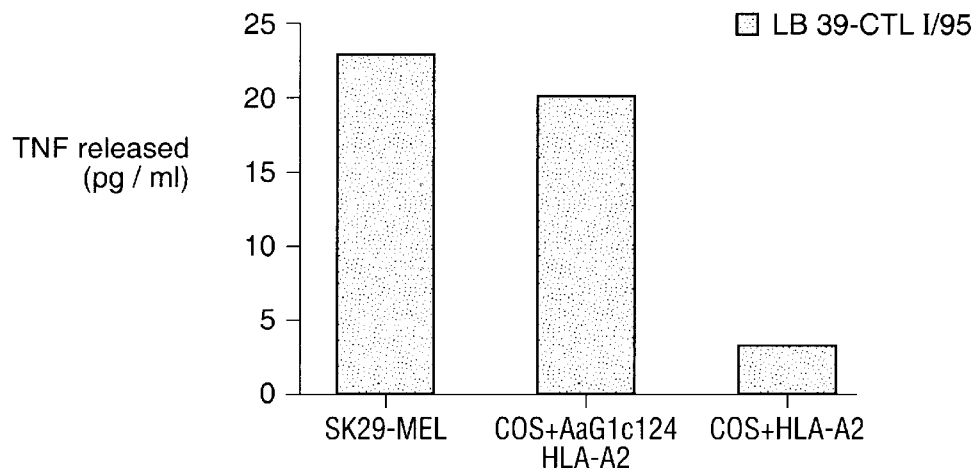
FIG. 3A shows TNF release induced by different cell lines, including transfectants, when tested with CTL clone I/95.

The two pools showing high yields of TNF in the supernatant were selected for further study. Specifically, the bacteria were cloned, and 800 bacteria were tested from each pool. Plasmid DNA was extracted therefrom, transfected into a new sample of COS cells in the same manner as described supra, and the cells were again tested for stimulation of LB39-CTL clone I/95. One positive clone was found, referred to as AaG1cl24. Convincing evidence that the transfected cells were recognized by CTLs was obtained by carrying out a comparative test of COS cells transfected with cDNA from the positive clone and the HLA-A2 gene, COS cells transfected only with HLA-A2, and cell line SK29-MEL. TNF release in CTL supernatant was measured by testing it on WEHI cells, as referred to supra. The optical density of the surviving WEHI cells was measured using MTT. FIG. 3A shows the results obtained with CTL clone I/95.

Figure 3B:
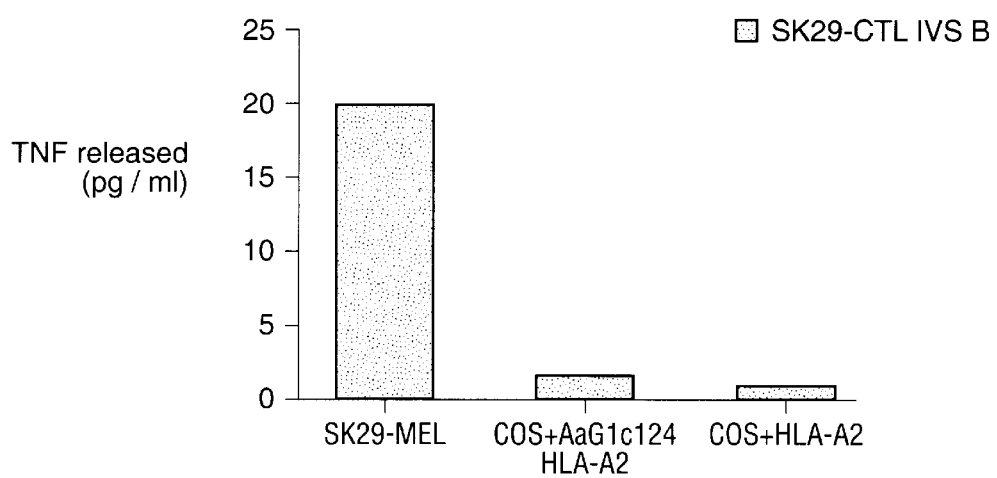
FIG. 3B presents TNF release data using CTL clone IVSB.

Further tests showed that the peptide presented by HLA-A2 in the transfected cells was different from that observed previously, i.e., a tyrosinase derived peptide. CTL clone IVSB is specific to complexes of tyrosinase derived peptide and HLA-A2. When this CTL clone was contacted to cells transfected with AaG1cl24 and HLA-A2, TNF release was minimal, as shown in FIG. 3B.

EXAMPLE 6

The cDNA from the positive clone was removed, and sequenced following art known techniques. A sequence search revealed that the plasmid insert showed no homology to known genes or proteins. SEQUENCE ID NO: 1 is a cDNA sequence representing the mRNA transcript of SEQ ID NO: 2, which is the full tumor rejection antigen precursor coding molecule, i.e., the genomic clone. The cDNA sequence sets forth a large, open reading frame at nucleotide positions 75 to 431.

The complete nucleotide sequence for SEQ ID NO: 2 has not yet been deduced. Much of it has. There is an uncoded region which follows nucleotide 9422 which is from about 4.7 kilobases to about 5.3 kilobases in length. This uncoded region is followed by SEQ ID NO: 12. As nucleotide sequence is inherent to a nucleic acid molecule, further details are not provided.

EXAMPLE 7

Figure 3C:
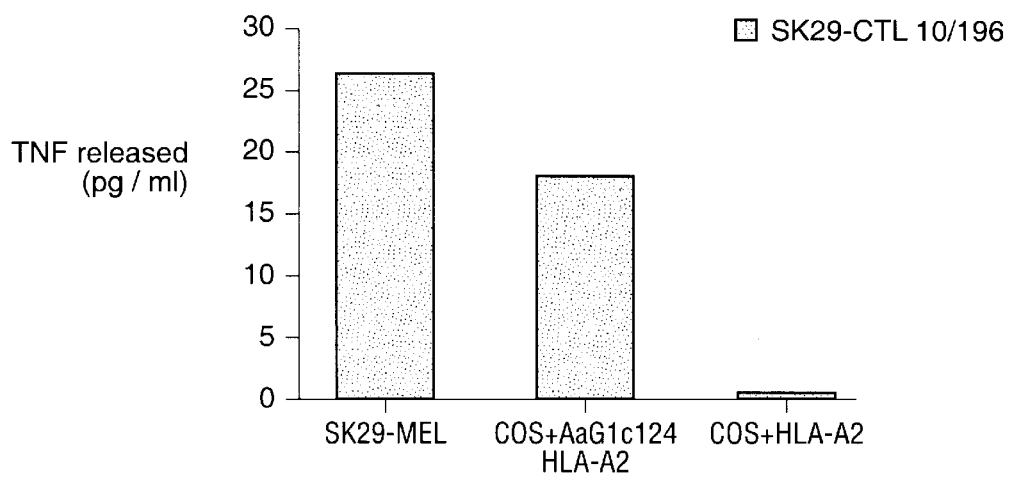
FIG. 3C shows TNF release using CTL clone 10/196.
Figure 5:
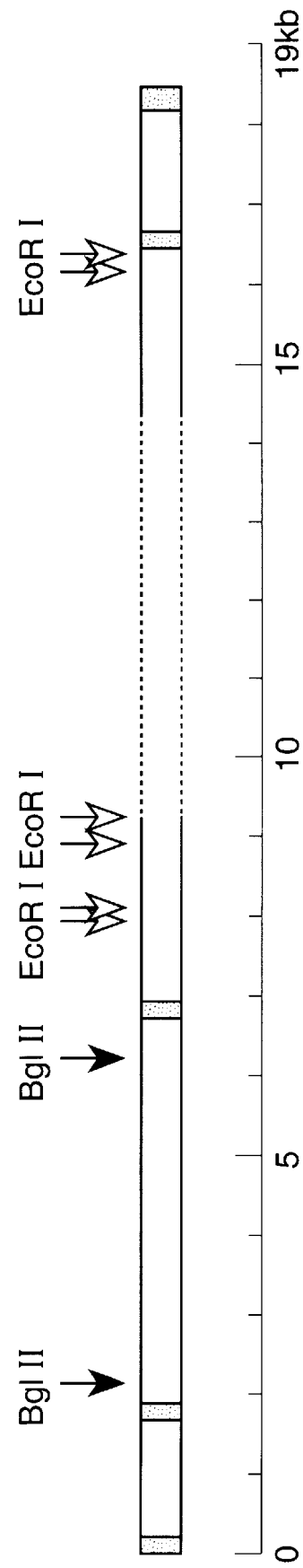
FIG. 5 sets forth, schematically, the structure of gene Melan-A, where exons are presented as black boxes, and restriction sites are depicted. Stippling represents unsequenced portions of the gene.

In the same manner that CTL clone LB39-CTL I/95 was isolated, a sample of PBMCs and a melanoma cell line developed from patient SK29(AV) were used to isolate CTL clone SK29-CTL 10/196. This new cell line was tested in the same manner as is set forth in Example 5. The results of the assays, depicted in FIG. 3C, show that the tumor rejection antigen coded for by AaG1cl24 (referred to as antigen "LB39-Aa" hereafter), is also recognized by this CTL clone. These experiments indicate that other patients can, and in fact do, generate CTLs specific for this antigen.

Oligonucleotide probes were derived from the described sequences, and were used in standard polymerase chain reaction methodologies to determine expression of the gene in normal tissues, tumors, and tumor cell lines. These results are presented in FIG. 4, and show that among normal tissues tested, only melanocytes expressed the gene. Note the expression in all tumor samples and/or melanoma cell lines tested.

EXAMPLE 8

The cDNA described supra is 675 base pairs long. It was used, as a probe, with total RNA of melanoma cell line SK29-MEL.1. A Northern blot was carried out, in accordance with Van den Eynde, et al., J. Exp. Med. 173: 1373 (1991), incorporated by reference herein, and identified a band of approximately 0.75 kilobases. Following this, the 675 base pair long sequence (SEQ ID NO: 1) was used to probe cDNA derived from SK29-MEL, using the same methodology elaborated upon, supra, for screening cDNA. A clone of 760 base pairs was identified, and SEQ ID NO: 3 sets it forth. The sequence differs from SEQ ID NO: 1 in having 83 additional base pairs at its 5'-end.

EXAMPLE 9

The gene corresponding to the cDNA described supra was then isolated. To do so, a genomic library of total human DNA (700,000 independent cosmids) was constructed in cosmid c2RB, using DNA from melanoma cell line LB33-MEL, following the methodology of DePlaen, et al., Proc. Natl. Acad. Sci. USA 85: 2274 (1988), incorporated by reference herein. DNA was isolated from 22 groups of 70,000 cosmids, and subjected to standard Southern blotting and hybridization, using as probe, $^{32}$p labelled SEQ ID NO: 1. The probe hybridized to nine groups. The group that produced the strongest hybridization band was subcloned, and then subjected to colony hybridization, again using the labelled cDNA. The cosmid which gave the strongest signal was then sequenced, using primers deduced from the cDNA sequence, viz:

OPC 69:5' GTA AGA GTG GCC GTG CCC CT 3' (SEQ ID NO: 4)

OPC 70:5' 5' CCA TCA AGG CTC TGT ATC CAT T C' (SEQ ID NO: 5)

OPC 71:5' ATA AAA GTC TTC ATG TTG GCA CTC 3' (SEQ ID NO: 6)

OPC 72:5' ACA GGT TCA CAG TTT TTC TCT TGA AG 3' (SEQ ID NO: 7)

OPC 73:5'GTA GGT CCG CTA GCA GTA C 3' (SEQ ID NO: 8)

OPC 75:5' AGA AGC AGT CTT CAT ACA CGC GG 3' (SEQ ID NO: 9)

The sequencing work revealed a first intron of 1512 base pairs, a second one of 5 kilobases, a partial sequence of the third intron, and a fourth intron of 1462 base pairs.

In further experiments, the cosmid DNA was digested with EcoRI and Bgl II, it having been determined from the sequences that these restriction sites were present in the gene. Oligonucleotides were prepared on the basis of each of the sequenced introns, labelled with $^{32}$p, and utilized in a standard Southern blotting experiment, using the digests referred to supra. This work led to hybridization of a 7 kb EcoRI fragment with $^{32}$p labelled oligonucleotides from the ends of intron 3. Estimated size of the intron was 9.5 kb, leading to a total length for Melan-A of about 18.5 kilobases. This estimation results from several datum, viz:

(i) the fact that in the Southern blotting work the oligonucleotide bound to either side of a 7 kb EcoRI fragment; and (ii) the fact that 2.5 kilobases of intron 3 of the gene had already been sequenced upstream of the EcoRI site located furthest downstream.

EXAMPLE 10

The pattern of expression of Melan-A was analyzed, using reverse transcription and polymerase chain reaction (PCR). To carry out the work, total RNA was isolated from tumor samples, following Davis, et al., (Basic Methods in Molecular Biology, 1986, New York, Elsevier, pp 310), or was secured from melanocytes.

Reverse transcription was performed on 2 ug of total RNA per sample, using an oligo (dT) primer. Samples of cDNA corresponding to 100 ng of total RNA ($10^4$ cell equivalents), was amplified for 35 cycles at 63° C. by PCR, using primers:

5'-ACTGCTCATCGGCTGTTG-3' (sense) (SEQ ID NO: 10)

5'-TCAGCCATGTCCAGGTG-3 (antisense) (SEQ ID NO: 11)

These primers are located in exons 3 and 5 of the Melan-A gene (SEQ ID NO: 2), and are used to exclude amplification of any genomic DNA contaminants. Aliquots of PCR reaction were run on 1% agarose gels, stained with ethidium bromide. To ensure that there was no degraded RNA, cDNA products were tested for the presence of human β action.

The results are presented in Table 1, which follows. Out of twenty-one melanoma cell lines, twelve were positive. With respect to normal tissue, only melanocytes were positive. Where skin biopsies were positive, it is presumed that this is because of a higher than usual proportion of melanocytes.

TABLE 1

Expression of the Melan-A gene.

| | Proportion of positive samples |
|---|---|
| Normal tissues | |
| Melanocytes | 2/2 |
| Skin | 2/3 |
| Liver | 0/1 |
| Kidney | 0/1 |
| Heart | 0/1 |
| Prostate | 0/1 |
| Breast | 0/4 |
| Ovary | 0/1 |
| Testis | 0/2 |
| Adrenals | 0/3 |
| Lung | 0/2 |
| Fetal brain | 0/1 |
| Cerebellum | 0/1 |
| *Substantia Nigra* | 0/1 |
| Tumors | |
| Melanoma samples | 26/26 |
| Melanoma cell lines | 12/21 |
| Breast tumor samples | 0/5 |
| Sarcoma samples | 0/5 |
| Non small cell lung tumor samples | 0/5 |

TABLE 1-continued

Expression of the Melan-A gene.

| | Proportion of positive samples |
|---|---|
| Renal carcinoma samples | 0/4 |
| Colon carcinoma samples | 0/4 |

The foregoing experiments describe isolated nucleic acid molecules coding for a tumor rejection antigen precursor, a "TRAP" molecule, in the form of genomic DNA, cDNA and mRNA. The protein molecule for which these code is processed intracellularly in a manner which leads to production of at least one tumor rejection antigen, or "TRA", which is presented by HLA-A2 molecules. While it has been observed previously that HLA-A2 molecules present peptides derived from tyrosinase, the nucleic acid molecules of the invention do not code for tyrosinase, and the TRAs are not tyrosinase derived.

The invention thus involves isolated nucleic acid molecules which code for a tumor rejection antigen precursor, or "TRAP", with the proviso that the TRAP is not tyrosinase such as, but not being limited to, SEQ ID NOS: 1, 2 and 3. The TRAP coded for is one which is processed to at least one tumor rejection antigen, or TRA, which is presented by HLA-A2 molecules on cell surfaces. The nucleic acid molecules of the invention may be, e.g., genomic DNA, ("gDNA"), complementary DNA ("cDNA"), or a form of RNA. The invention also involves isolated nucleic acid molecules which are complementary to the molecules described above. An especially preferred form of the invention are molecules which contain the sequence set forth in SEQ ID NOS: 1, 2 and 3.

Also encompassed by the invention are vectors which contain the nucleic acid molecules of the invention, operably linked to a promoter. The vectors may also include a molecule coding for HLA-A2. As these two molecules, i.e., HLA-A2 and the TRAP, are necessary to generate a cytolytic T cell response, the invention also encompasses expression systems where nucleic acid molecules coding for TRAP and for HLA-A2 are presented as separate portions in, e.g., a kit. The invention also encompasses cell lines transfected by the vectors described herein, be these prokaryotic cells, such as E. coli, or eukaryotic cells, such as Chinese hamster ovary ("CHO") or COS cells.

As indicated, the complexes of TRA and HLA-A2 provoke a cytolytic T cell response, and as such isolated complexes of the tumor rejection antigen and an HLA-A2 molecule are also encompassed by the invention, as are isolated tumor rejection antigen precursors coded for by the previously described nucleic acid sequences.

The invention as described herein has a number of uses, some of which have already been described. First, the identification of a tumor rejection antigen which is specifically presented by HLA-A2 molecules, as well as a nucleic acid molecule coding for its parallel tumor rejection antigen precursor permits the artisan to diagnose a disorder, such as melanoma, characterized by expression of the TRAP. These methods involve determining expression of the TRAP gene, and/or TRAs derived therefrom, such as TRA presented by HLA-A2. This can be accomplished by using the recited sequences, or fragments thereof, as probes, primers, and so forth. Other TRAs may also be derived from the TRAPs of the invention and presented by different HLA molecules. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred.

The isolation of the TRAP gene also makes it possible to isolate the TRAP molecule itself, especially TRAP molecules containing the amino acid sequence encoded by SEQ ID NO: 1. These isolated molecules, when presented as the TRA, or as complexes of TRA and HLA, such as HLA-A2, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular.

Therapeutic and some diagnostic approaches presented in this disclosure are premised on a response by a subject's immune system, leading to lysis of TRA presenting cells, such as HLA-A2 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 7, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR. This diagnostic approach need not be, and is not linked, to the previously stated therapeutic approach, as a diagnostic method is per se useful.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-A2 presenting cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated genomic DNA molecule which encodes a tumor rejection antigen precursor and which hybridizes to a nucleic acid molecule consisting of the nucleotide sequence of SEQ ID NO: 1, under Southern hybridization conditions.

2. The isolated genomic DNA molecule of claim 1, consisting of from about 18 to about 18.5 kilobases.

3. The isolated genomic DNA molecule of claim 1, comprising the nucleotide sequence of SEQ ID NO: 2 or the nucleotide sequence of SEQ ID NO: 12.

4. The isolated genomic DNA molecule of claim 1, consisting of, in 5'-3' order the nucleotide sequence of SEQ ID NO: 2, followed by about 4.7–5.3 kilobases, followed by the nucleotide sequence of SEQ ID NO: 12.

5. Recombinant expression vector comprising the isolated genomic DNA molecule of claim 1, operably linked to a promoter.

6. The recombinant expression vector of claim 5, wherein said isolated genomic DNA molecule comprises the nucleotide sequence of SEQ ID NO: 2 or SEQ ID NO: 12.

7. Recombinant expression vector comprising the isolated genomic DNA molecule of claim 4, operably linked to a promoter.

8. A prokaryotic or eukaryotic cell line transformed or transfected with the isolated genomic DNA of claim 1.

9. A prokaryotic or eukaryotic cell line, transformed or transfected with the recombinant expression vector of claim 5.

10. An isolated nucleic acid molecule which encodes a tumor rejection antigen precursor having an amino acid sequence encoded by the nucleotide sequence of SEQ ID NO: 1, SEQ ID NO: 2, or SEQ ID NO: 3.

11. The isolated nucleic acid molecule of claim 10, comprising the nucleotide sequence of SEQ ID NO: 1 or SEQ ID NO: 3.

12. The isolated nucleic acid molecule of claim 10, the nucleotide sequence of which consists of SEQ ID NO: 1 or SEQ ID NO: 3.

13. Recombinant expression vector comprising the isolated nucleic acid molecule of claim 10, operably linked to a promoter.

14. The recombinant expression vector of claim 13, wherein said isolated nucleic acid molecule comprises the nucleotide sequence of SEQ ID NO: 1 or SEQ ID NO: 3.

15. A prokaryotic or eukaryotic cell line, transformed or transfected with the isolated nucleic acid molecule of claim 10.

16. A prokaryotic or eukaryotic cell line transformed or transfected with the recombinant expression vector of claim 13.

17. An isolated nucleic acid molecule, the nucleotide sequence of which consists of the nucleotide sequence of SEQ ID NO: 10 or SEQ ID NO: 11.

18. A method for diagnosing a disorder characterized by expression of a tumor rejection antigen encoded by a nucleic acid molecule which comprises at least one of SEQ ID NO: 1, SEQ ID NO: 2, SEQ ID NO: 3, or SEQ ID NO: 12, comprising contacting a sample with at least one nucleic acid probe which hybridizes to mRNA for at least one of SEQ ID NO: 1, 2, 3 or 12, and determining hybridization of said nucleic acid probe to an mRNA target as a determination of said disorder.

19. The method of claim 18, wherein said method comprises polymerase chain reaction.

20. The method of claim 18, wherein said nucleic acid probe has the nucleotide sequence of SEQ ID NO: 10 or SEQ ID NO: 11.

21. The method of claim 18, comprising contacting said sample with two nucleic acid probes, having the nucleotide sequences of SEQ ID NO: 10 and SEQ ID NO: 11.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 676 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

| | | | | | | |
|---|---|---|---|---|---|---|
| TCTTCATACA | CGCGGCCAGC | CAGCAGACAG | AGGACTCTCA | TTAAGGAAGG | TGTCCTGTGC | 60 |
| CCTGACCCTA | CAAGATGCCA | AGAGAAGATG | CTCACTTCAT | CTATGGTTAC | CCCAAGAAGG | 120 |
| GGCACGGCCA | CTCTTACACC | ACGGCTGAAC | AGGCCGCTGG | GATCGGCATC | CTGACAGTGA | 180 |
| TCCTGGGAGT | CTTACTGCTC | ATCGGCTGTT | GGTATTGTAG | AAGACGAAAT | GGATACAGAG | 240 |
| CCTTGATGGA | TAAAAGTCTT | CATGTTGGCA | CTCAATGTGC | CTTAACAAGA | AGATGCCCAC | 300 |
| AAGAAGGGTT | TGATCATCGG | GACAGCAAAG | TGTCTCTTCA | AGAGAAAAAC | TGTGAACCTG | 360 |
| TGGTTCCCAA | TGCTGCAGGT | GCTTATGAGA | AACTCTCTGC | AGAACAGTCA | GGACCACCTT | 420 |
| ATTCACCTTA | AGAGCCAGCG | AGACACCTGA | GACATGGCTG | AAATTATTTC | TCTCACACTT | 480 |
| TTGCTTGAAT | TTAATACAGA | CATCTAATGT | TCTCCTTTGG | AATCCTGTAG | GAAAAATGCA | 540 |
| AGCCATCTCT | AATAATAAGT | CAGTGTTAAA | ATTTTAGTAG | GTCCGCTAGC | AGTACTAATC | 600 |
| ATGTGAGGAA | ATGATGAGAA | ATATTAAATT | GGGAAAACTC | CATCAATAAA | TGTTGCAAAT | 660 |
| GCATAGTAAA | AAAAAA | | | | | 676 |

( 2 ) INFORMATION FOR SEQ ID NO: 2:

( i ) SEQUENCE CHARACTERISTICS:
        ( A ) LENGTH: 9421 base pairs
        ( B ) TYPE: nucleic acid
        ( C ) STRANDEDNESS: double
        ( D ) TOPOLOGY: linear ( i x ) FEATURE:
        ( D ) OTHER INFORMATION: Following position there is an
            unsequenced portion of from 4.7 to 5.3
            kilobases ( x i ) SEQUENCE DESCRIPTION: SEQ ID NO: 2:

| | | | | | | |
|---|---|---|---|---|---|---|
| CCGTCAGAAA | TCTAAACCCG | TGACTATCAT | GGGACTCAAA | ACCAGCCCAA | AAAATAAGTC | 60 |
| AAAACGATTA | AGAGCCAGAG | AAGCAGTCTT | CATACACGCG | GCCAGCCAGC | AGACAGAGGA | 120 |
| CTCTCATTAA | GGAAGGTAAG | AGCGTTGCCT | TCTCGCCATA | ATCATAGTCC | TCTTCTCCCA | 180 |
| GAATAGGATT | TGGGAAATTC | TGGCTAAGTC | CTCTGCCTAC | CCTCATTGCC | CCGCTGATGT | 240 |
| GTGACATCAA | CAGAATTTCT | CCGCAACGTT | TGTCAGTCTC | CAACCTCAGA | GGGCTCACAA | 300 |
| AGCCTCCTCC | TGAATCCTCT | CTCAGTCCTC | CAACACTACC | AAGAAGAAAA | GCAATTATTC | 360 |
| AGGATGGCAT | CTTGCTGGGG | AGAAGCAGCC | TCCCTGAGGT | AGATGTGTTC | TCCTGTCACT | 420 |
| TAAAGAACCA | CTTCTCCTGG | TCTGAGTAGT | AAGAGGCGCA | TTTGCTGTTG | CTGCACCATT | 480 |
| TGCCAAGGCT | CTGAGTTTGA | GGTATGGGAT | GTATTAAAAC | AATTTAATGA | AGAATTAAGA | 540 |
| TTCCATTCTG | TCATTTTGAA | CACAGGGTTC | AGTCCTATAT | TATTCACTTG | AGAGGACTGG | 600 |
| TGAGTTTGAC | TTTCATTTCT | TTTTACAAC | TGGGAAGGGC | AAATTACACA | TAAAATGTCC | 660 |
| CAGTGGAAAG | GGGTCATGTG | TCGAAATCCC | CACTCTTCTG | TCTCACCTCT | CCCTGTTGTT | 720 |
| TTAAACTGGG | GCTCATTAAT | ATAATTCTAT | GGGGATCACA | CCTTTGAAAT | TCATGAGGAC | 780 |
| AGTAAGAGAG | CAGAAAAATA | CACAATAATA | AGGAAGGAG | CTTCCATTAT | TGGTTTTAA | 840 |
| TGAGCGTACT | TGAATTACGG | CCACTGCaGT | TTATGGATAT | TTTTTGTTGT | TCATTTGTAT | 900 |
| GTGTTATAGT | TAGAAAAAAA | AAGAATCCTA | GCCAAGGGAC | TTGAACCAGA | GAAAGCAGA | 960 |
| AATTGACTTA | AGTAGGAAGG | GAAACACATT | ATTAGATAAA | GTCAGGTCCT | GGGCTTCCTC | 1020 |
| GGCTTGTTTT | GGGTGGAGTG | CCTGGGGACA | GGCTGAAGCC | CCTGTGTGGG | GTGGTTTCCT | 1080 |
| TTGCTGAAAA | GCTGGGCTGG | AAGATGTTGT | GCTCAGTGCT | CAACCTCATG | CACCCTCGCG | 1140 |

```
AGGCACAGGC  AACGGGTGCT  CTGGGAAACA  CACGTTATGT  ATCATAGCCT  CTGTTTGTCT   1200

GTGGGATTGA  TATCCAATAA  TAACTTTGGA  GAAAATAAC   TCCTCTTATT  TTGTTAGCCA   1260

CAGCCCTGGG  CCAGGGAAGG  TGGAGAATCA  GTGAAATGC   ATTTTGTTTG  TTTCTCTAGA   1320

AGTTTATGGT  GCAGAGTCAA  ATTGAAGGCA  AATGAGGAAT  ATTTTTTCAT  TAAATAATAA   1380

CTCAACTTGC  AAGTCTTTTT  TGCTTTTGTT  TGTAGTTTCT  TCTTTGAACT  TAATTTTCAG   1440

TTAGTAGGAG  GGGTTAGAAA  CCTGAGCTAT  TGCTAAAGCC  CTTGATATGA  ATGAAAGAAG   1500

CAGGTGCAAA  TCCCCTCACA  GAGAGAAACC  AAAGGGTCCT  GGCTATGGAT  ATTGGTCACC   1560

TAGTCAGGAT  GCTGTTGTGG  GTCTTTATGA  GATGATGAAT  AGGGTGGCTT  TGGATGCATT   1620

AATGATATTT  ACATGCTCCT  TCTGTTAGTG  TCCTGTGCCC  TGACCCTACA  AGATGCCAAG   1680

AGAAGATGCT  CACTTCATCT  ATGGTTACCC  CAAGAAGGGG  CACGGCCACT  CTTACACCAC   1740

GGCTGAAGAG  TAAGTTCAAA  ACCAGACCCA  GCAGGGCTTC  CAGTTTGCCG  TTTGCTGACA   1800

CAGCCTGCTG  ACTTCCACCA  GTACATGCCT  GCTCGTAAAT  CTCCCTAGTG  TTTATCTCCC   1860

CAGACAGTAA  CATCCCTGGC  AACAAGGGGA  GGAGATTCTG  TGCTTCTATA  AGGGGCTCAG   1920

TCAAGCTTCT  CTGAGGCCAA  ACAGGCAGGA  AGATGGGAAT  GGTATAAGGT  TGGATCTTGC   1980

CATTTTTGGG  TGCACTTTTG  ACTATTGGGT  CTTATCTGTA  GGTTCCCAAG  TGGAAAAACA   2040

TCTGTTCAGG  ATCACAATGC  CTCTCTCCTC  AATCCTTGTT  CTGTCTCCTC  CACTCAAATT   2100

CCTGAAGGTG  GTTTGCAGAC  AGAATAAAAG  TGAGTTGCCA  AGGAGCCAGT  AAGGATGACG   2160

GGCAGGTGTG  TGTGACTCAG  CCCACAGCCA  GACTCGAGAG  GAAGATGGAG  GTCACAGCCT   2220

TTGCAGTATA  ACTTTATCCT  AAGGAAAGAC  ATTGGGTTTT  ATGAGTGAAT  TAAAATAAG    2280

TATTTATATG  ATTAAGCATT  TCTAAATGCT  AAGCATTGTA  TACTGGCGTG  AGACACTGTT   2340

TTTATCTTTG  AAAAAACTCA  CAACTTAGTG  GGAGAGTTAG  GCATGAGATT  AATTTCAGCA   2400

AATGTAAGTG  CGGTAATGAA  AACCCAGAGG  CTGCAGGGAC  ATACTCTGTA  TGTGCTGGGA   2460

GTGGGAAAGG  GACATACTCT  GTACGTGCTG  GGTGGCAGGG  GCAGGGAGG   CCCCACCCTC   2520

TGCGTGGGAC  TGTAACAGGA  CAACACCCTC  TTATGTGGTC  TGTCCAGAAC  TCCCTGTGAA   2580

CCTGCTCTTT  CTTTGGAAAG  AGCTGTTGAA  CAATCTTTGT  TAACAGTCAA  CCGCAGGACC   2640

AGCAAGATGT  AAAGCCCAAC  AAAGGCACTG  AGGAAGAGTT  CAGGNAGACA  GCATTTCCTC   2700

AGAAGACCCT  GGTATAGGAT  CCTCTAATAT  CCCTGGCCAA  TTGGAGATGA  GGGCGGCGGT   2760

ATCCTCTCAG  AAAATGTCCT  GACAGCAAAA  ACATACTCTT  TGAGGGAGGG  GAGCCCATTG   2820

CCCGTGCTAT  TAGTTAGGGT  ATCGTTTCAG  CTTGTGTATA  ATCACTCAAC  AGACTCTTTA   2880

AAATATACTT  TTATGTCTCG  TGTAAAAATT  CAAGAGTAAA  GAGTTCAAGG  CCTGTTCGTT   2940

TTCTTCTTGC  TGGTTACTCC  CTTGGGATCG  TCACTTTTGT  CCCCATGGCT  GAAGATGTTG   3000

TGCCATCACC  TCCACATCTT  GCCAACGAA   AGCAGGAGGT  GAAGGAGAGG  CTAGGACCAT   3060

TCCTTTCAAG  GGGCACACGT  CACTTCTGCT  TATTGCTCCA  CCCCCGCCCC  CCGCCCCGTG   3120

GCACCCACCC  TGGTGGTATC  ATTCTTGCTG  TGTTGTAAAT  GAAGAAAGGT  TTAGAGAAAT   3180

TAGGAAATGT  GTGGCCAGAC  ATGGTGGCGC  TGGGATTTAA  ATCCAGGTCT  GTTTGCCTCC   3240

AGAGTCCATG  CTCTTAAGTG  TTATGCTGCA  GGCCAGCAGA  GGCAAATATT  TGCACAATCC   3300

CATCCGACGA  GAGGCTAGGG  CAGAGGTCAG  TATCTCTCAG  TGTGAAGCTG  GAGGCTGATG   3360

CTAGTCAGCT  CAGTAGGCCG  AAAGTGGAGT  TGTCCTTTGC  CATGTAGGGC  CATCATGCCC   3420

AGCTGGGGAA  CCTCATAGCC  AGGTGTACCC  ACAACCTGAA  CAAGGTAACT  TTCAGGGTCT   3480

AGTCAGGAAG  AAACCAACTA  GATGGTTCAA  CATAGAGACT  TTAATATAAG  AAGCTGGTTA   3540
```

```
AACAGGCATG  GGACTGAGAC  TGAGGAGGCA  AAGAAGGCAT  CGGGGCAACC  AAGGCTGTAC   3600

CCACAGAATG  CTGCTTCTAC  CCCCGTGTCT  GGGGTAACAA  ACGGAAGGGT  GAGGCCATCA   3660

GGACCTAGAG  TTGGGAGGAG  GGACGCCACA  GAAATGGGAC  CCAGATCTCT  AAGGAGAGAT   3720

TTTTGTTTGG  CTGGTTCTGG  TGTCTCAAGA  GCTTAGAAGT  GAGGGGCATG  AATCAAATAC   3780

TCAGGCCTCT  GAGGTCAGCC  AGTGCTCTGC  TGGGGAGGGG  CATAATGAAG  CTGGCTCTGA   3840

CAATGCCGGA  AAACGAGCTG  GTGCTTGGCA  TATACAGACA  ATGTGAGCAT  TGCTGGGGTG   3900

ATCCTGACAG  GAGCCAGAAG  CACACTGGAA  GGAGCTGCTC  CTTCTTGATG  CCCCAGGTTT   3960

GTAGGCACCC  TCTAGAGTAC  TCTAATGGGA  GCCAGTGGGC  AAAGGAGAAG  TGGCATTTGC   4020

AGAGTCCAGT  CCCAGCATCA  CAGAGCAGAG  CATAGAAAGG  TAGGTTTGGA  GAAGAGGGAC   4080

AATGGCTTAA  TAAAGGGCAA  AGGGGGTTAT  GACCACTATC  ATGTGAAGGA  ACCCCTTGAC   4140

TGAAGGCACA  AGCTTTCTGT  GTCTTGCAAC  CTGAATGACG  TGCATAAGCA  GGGTCAGGTG   4200

GGTTATCTGA  CATTTTCCTT  GAGAACAAGA  GGGAGCCTCT  GGATTCCAGC  ACAAAAGAAA   4260

AATACCCACT  CAACCCGTAT  GCGTGGGAGC  TATCCTTTAA  AGAGAAAGTA  ATTCCTTTTG   4320

ACATTTGCT   GTCTGTAGAA  GGGTCAGATG  GCCAAAGCTT  CCAGCACAAT  GAAACACTTA   4380

ACTTCAGTCT  GTGAGTGTAG  GAACCCCTGA  ATACATGGAA  CATCATCATC  TTGTGCAGGT   4440

ACTGAAGGAG  ATCGGTCCAG  AAAATAAGTA  ACTGCACATG  GCCACCAATG  TCAAAAGTCA   4500

TTCCTCTCAT  GAAAAGTCCC  TGCCCCCATT  GCTGTTTGTT  TAAATAGGTG  GGATGGAGGT   4560

AGGGGAATGG  GGCCATCTTC  TTTTTTTTTT  TTTAATTTTT  TTGCATAAAA  TCCAGATCCT   4620

GCACAATGGG  GCAATCTTCA  TTAAACAAT   GCATCCCTAA  GATCTGAGAA  TATTTATCCT   4680

TCTCACAATT  GTGCCAGCAG  GTGGAATGAA  GAAGAATGAT  GCAAATAAG   TTCCCACATC   4740

CAGCCAAGAA  GGACTACATA  CCTGCTTTGG  GTATTATGTA  TCCCTTTGAA  ACCTCAGTGG   4800

AGAGCAGTTC  TCACAGTTGG  GTGGACACAA  GTCATCCATG  GAACTTGTTA  AAATGCAGAT   4860

TTCTAGGTGC  TGCCACCTAA  GAGGCTGATT  GGGTAGGCCA  GGGGTGGAGT  CCTATGATCT   4920

GCACCTTAAC  GTGCATCTCA  GGTGATTCTG  CTGCAGGTGG  TATTTGGAAG  ACACTCTGAG   4980

GCGCCCTGCC  AAGCTGGGCA  GTGGGTTCTT  CCAATGTGTC  AGGCATACCC  TGGTGCTTTT   5040

CGCTCTCAGT  CACTTGGGCA  TGTTGTGAGT  ACCACGTGAC  CATGCATAAA  GTGCTGTAAC   5100

AGAGCTCTGT  CTGTGTCAAG  ATATTCAAGT  GGACGCCACA  GGGTAAAATG  AGAGCACAGG   5160

CATGTTGGGA  GTTGAATCAG  CTGCCTTCAG  TCACGAGAAC  ACACTGAACA  CTCCTTGTGA   5220

CAGCTTCAGT  TCAGGAAAGA  GTGACTCTGC  AGGAAAAGCA  CTGGCCTGGG  AGACCTGGAT   5280

CTGGCCCAAA  TTCTGGTGCT  CACTTGCTTG  GTCTCCCGTT  CCAGTTGCTG  TGAATGTTGG   5340

TTCTGCCACT  TGCTGGTTGT  GCAGCCCTGG  GCACTTGACC  AGCATAATGT  CAGCTGTAAA   5400

ATGAACATCA  TTCCTAACTC  CGAGGACTGT  GGTTAGGATG  AAATAAAGC   ATATATGTGG   5460

GGGTGCCTAG  CCCAGTGCCT  GGCACAAATT  GGTGCTCAAT  GAATGGTAGT  CACTATGGTT   5520

ATGGTAATGT  TGATGAATCT  TCATAGGTCT  CAGCTTCCTG  ATCTATAAAG  CGGGTGGACT   5580

GACCTACATA  AGTCAGAGTT  TCCATCTAGC  ACTGTCATCC  CATGGTTCGC  TCTATCCTGT   5640

TTGGAGACGG  ACAGGATAAG  CTTGATGTCT  CCTCAGCCTT  GAGACAGAAG  TTGTCCAGTA   5700

GATGGTACTG  AGCAAAAGTC  TCTCCAGCAG  AAGCCTTAGT  TAAACCTTGC  TTCTCCTGTA   5760

GCTGCTCAGT  CTCTTGTAAG  TCACTCAGCT  CTGCAGAAAC  TTTCTTAGCG  AGTTGACAAC   5820

CACAGATAAC  AGAGTCAGTT  CTGTCGATTT  TGATCATGCT  GTGATCAGGC  AGATGTTAGC   5880

TAATTGATGA  TGCTTGCCCG  GAGTGAACAG  CTCCAGGCCC  TGTTTCCAGG  GTCTTTGTGG   5940
```

```
TAACTTTGTG  GTAACTGTAA  TGCTTCCCAG  GGGTCACTGA  ACACAGGGCC  CAAGAGGCTG   6000
GTGTAGACCC  CCAGATTGGC  ACCCTGCTGC  TTAGACAAGA  TCCTTCTCAA  TAAGTAATGC   6060
CATAGCTTTG  CTGTAGGTTC  AGCCCAGACA  CTTCTCCCTA  GGGCTGCAAG  GAGCAAAGCG   6120
GGGAGTTTAG  GGAAGGGAGG  GCACGAACAT  AATTGAGACG  GATTCAGGTT  CAAATCCAGC   6180
CTCTGTTTTG  TGCTAGCTCT  GTATGATCAC  CAGCGAGTCA  TGTATCCTCT  GCCTTTTATT   6240
TCCTCTTCTG  TGAAAATAGG  GGATGATAAA  TTGTGTCTAC  CCTCCAGTGT  TGATGTGAGA   6300
ATTGAATAAG  CTAATGAATG  TTTAGCACAG  CACCTGGCTT  TTAGTAGATG  AGTCAGTGTT   6360
AATTTCTATT  TTCTCTTTGT  GGGCTGAGTT  GGAGAAAATG  TTTTAAAACA  GCCTGATGAG   6420
AAGAAAAGAT  AATTTAGCCC  CAATAAATAC  ATTGTCCACA  TAAAGACAGT  TACTATGGCA   6480
CTTCTCATAC  CTGGAACTTG  GGTGCCTGGG  CCATGCAATT  AGCAGAGTTC  CTGTGGGCAC   6540
ACACTTGAGA  GGCTCCTAAA  GACCTGGGTT  AGATCCAGGT  GCTGGAGGCC  TGGTGGGGTG   6600
CCAGTGTGGG  AGGTGGGAAA  CTACTTGGAC  ACTGGGAGAT  GCTGCTCTGG  GTCGTCAAAG   6660
TCCATATGAA  GAGGAAGACT  GATTTATGCT  TCATCATAAT  GTAGAACAAT  GTTTCAATGA   6720
CAAAGTGGAT  TTGTCTATCT  CTTGGGCCAG  GCCGCTGGGA  TCGGCATCCT  GACAGTGATC   6780
CTGGGAGTCT  TACTGCTCAT  CGGCTGTTGG  TATTGTAGAA  GACGAAATGG  ATACAGAGCC   6840
TTGATGGTTG  GTAAAGTTCC  CACTGCTGAA  ATCCCTCCAA  GTCCAGGGCC  CTCTTTCCAG   6900
TTCTTTCCTC  TGAATCTCTG  GAGAGTCAGA  TAATTGCCTC  ATTATAACCT  TCAGCTCTGA   6960
TTCCGGCTTC  TGATGCCTCT  TTTGCTACAT  TGTACTTTGG  CAACTCTACC  TTTGCCTCTG   7020
CTCAGGCATG  AACCTCAACC  AGGAACTTGC  CCTGTGTCTT  AGTCTGTGAT  TATAACATAA   7080
TACGAGAGAC  TGTAATTTAT  AAATAAATGA  AATTCATTTG  GTTTACAGTT  GGGAGGCTGG   7140
GAACTCCAAG  ATCTAGGGGC  CACACCTGGT  GAGGACTTCT  TGCTGTGTCA  TATCATAGTG   7200
GAAGGCATCA  CATGGGCAAG  GGAGTGAGAG  AGCAAGAGGG  AGCTGAACTC  ATTTTTTTTT   7260
TTTCTTGAAA  CAGGAAATCC  TGGGATGGAG  CGCAGTGGTG  ATCATGAGTC  ACTGTAGCCT   7320
TGACCTCCTG  GGCTCAAGCC  ATCCTCCTGT  CTCAGCCTCC  AGAGTAGCTG  GGACCACAGG   7380
CACGTGCCAC  CACACCGGCT  AATTAAAAAA  AAACTTTTTT  TTGTAGAGAC  GAGGTCCCAC   7440
TATGTTGCCC  TAGGCTGGTC  TCAAACTCCT  GGGCTAAAGT  GATCCTGCCT  CGGCCTCCCA   7500
AAGTGTTGGG  ACTACAAGTG  TGAAACACTC  CACATATGGC  CCAAACTCAC  TTTTATAACC   7560
AACCTACTTT  TGCAATAACA  AACACACTCC  TGCAATAACA  CAATTAATCC  ATTCGATGAG   7620
GACAGAGCCC  TTGTAACTTA  ATCGACCTCT  TAAAAGTCCT  GCCTGTTACC  ATTGTTGCAT   7680
TGGGGATTAG  GTTTCCAATA  CACGAATTTT  GGGGGACACA  TTCAAACTAT  AGCACCTGTC   7740
TCTTTGGTTC  TACTCATAGC  AGACTTGGGT  ACCTGGATGT  TGTGTGTAGC  TAAGCACTGA   7800
CGGTTTATAG  GGCACAGGGG  AAGGGGTTTG  AGGTTCCCTT  ATAGCAAACA  GGAGTATATT   7860
AGACACCTCA  GGTTTTACCA  CTTCTGGGAA  TTCTTGCTGG  TTCTGTTACT  CCACTTTGTG   7920
ACCTGCTCTT  CCTACTTTTC  TTCTTCACCC  CTTTCCTCAC  TGGTTACCTG  TGAATTCCAA   7980
GTTCTTCTGA  CTCTACACTA  AGCATCCCAG  GATATCATCA  GTGCGATGAG  GAAACCATCC   8040
TTCCTGCATC  AGCACAAAGG  GTCACTTGTG  TGTTTTTTAA  CAGGCTGCAT  CCTTCTTAGA   8100
TGGCCAAAGG  TTTTAATAGT  ATTTTTTTCT  TCTTTACCCA  AATATGCAGG  AAGCTAACAC   8160
AATTACACAA  TCCAATCTTC  TGGTACCAGT  ATCCTCCATG  AATGGGAAAC  ATCAACTGAG   8220
TTTATAAGCT  ATAAAAATTA  CAGGTTTCAG  CAATCTTGCT  TAAAGCCAGG  TAGCACTTCA   8280
GCACTTCAGC  ACCCGAAGCA  TTCTCCATAG  ATCTCGCTGT  CTCTCTTTCT  TGTTATTACA   8340
```

```
GATCTGAAAG CTTTTCAGGT TGATGCATAA TGGAAAAAAA GTATCTTTCC AAAAGATGTT    8400
GGAAAGTCCC ATTCTCATTC AGCAAGCACT TCATTTAGAG GAAAAGGTCC TGTGAAAGAG    8460
AGGAGGGTTG GTGTGGGGTG GGGATTGAAG CTTGGCAAGC TGATAAGGAG AAGGTGAGAG    8520
ATACAACTCT GGATTCTTTC CCTCTTTGCC AAGAAACTTG GGCAGTCTCA TGTCTCATGT    8580
CTCCTGTTCC CCAATGTCTT TCCAGAGCAT AAATACAAAT ACAAACCATC AAAGGCAAGT    8640
CAAGTCTGGG GGCTGACACA CCCACCGAGC ATAGCCCTCT AGTGTGCTGA CATCTAGTGG    8700
GAAGGAGGAG GAGTTGATGA ATCTGAACAA GACTCCAATA TTGGAGGAAA TACTTGAGGA    8760
AAGCCTTGGG TTAGAAAGTT AGGGATAGAA TTCCTGCTCA TACGGCTGTC CACAACAGGT    8820
TAGTAGGGGA GGACTTTAAT CTCTGCCATA GAACTCCATT TGTAACTCTA GCATGGGGTT    8880
ATGACATTGC CTTGTAATTG GCTATTTACT TTTGCCTCT TCGACCCCTC CGCTTTCCCC     8940
TATGTATGAA CCACAACAGA GAATATTTCT AACTCATCTT CATATCTCCA GTGCCTAGCA    9000
CAGTGCCTGG TACATGGTAG TCACTCAATT GTGTTGCATT AGGACTTGGT CCCATTGTCT    9060
GCCATTGAGT TGCTTGGAGA CTAGAATTCA ACTTCTCCAA GATTCACTAG CTCTATTTTA    9120
CACCCAGACA TGTTGGAAAT CTGTGATGTA ACACAATGTA TATCCATTTT TATTTAATAC    9180
ATATTTTCTT CTATATTTTG ATTTCATTAT ATATTTGTAT ATCAAAACA AAATGTTTAG     9240
TCTTTCAAGA AGTAAAGCTA TACAAACTCA ATATGTTGGT ACTCATTTCC TAACTATAAT    9300
TATTAGTTTG ATCCTATTGA ACACAAATGC AGTAATTTTT CTTTCTGCT TCAATGCTCT     9360
CATCTTAAAT TCATTTAATT GAAAAATAAC AGAGAGTCTT AATGTCATGT GCTCAGACAC    9420
T                                                                    9421
```

( 2 ) INFORMATION FOR SEQ ID NO: 3:

( i ) SEQUENCE CHARACTERISTICS:
        ( A ) LENGTH: 760 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
CCGTCAGAAA TCTAAACCCG TGACTATCAT GGGACTCAAA ACCAGCCCAA AAAATAAGTC      60
AAAACGATTA AGAGCCAGAG AAGCAGTCTT CATACACGCG GCCAGCCAGC AGACAGAGGA     120
CTCTCATTAA GGAAGGTGTC CTGTGCCCTG ACCCTACAAG ATGCCAAGAG AAGATGCTCA     180
CTTCATCTAT GGTTACCCCA AGAAGGGGCA CGGCCACTCT TACACCACGG CTGAACAGGC     240
CGCTGGGATC GGCATCCTGA CAGTGATCCT GGGAGTCTTA CTGCTCATCG GCTGTTGGTA     300
TTGTAGAAGA CGAAATGGAT ACAGAGCCTT GATGGATAAA AGTCTTCATG TTGGCACTCA     360
ATGTGCCTTA ACAAGAAGAT GCCCACAAGA AGGGTTTGAT CATCGGGACA GCAAAGTGTC     420
TCTTCAAGAG AAAAACTGTG AACCTGTGGT TCCCAATGCT GCAGGTGCTT ATGAGAAACT     480
CTCTGCAGAA CAGTCAGGAC CACCTTATTC ACCTTAAGAG CCAGCGAGAC ACCTGAGACA     540
TGCTGAAATT ATTTCTCTCA CACTTTTGCT TGAATTTAAT ACAGACATCT AATGTTCTCC     600
TTTGGAATGG TGTAGGAAAA ATGCAAGCCA TCTCTAATAA TAAGTCAGTG TTAAAATTTT     660
AGTAGGTCCG CTAGCAGTAC TAATCATGTG AGGAAATGAT GAGAAATATT AAATTGGGAA     720
AACTCCATCA ATAAATGTTG CAATGCATGA TAAAAAAAAA                           760
```

( 2 ) INFORMATION FOR SEQ ID NO: 4:

( i ) SEQUENCE CHARACTERISTICS:

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 4:

GTAAGAGTGG CCGTGCCCCT                                                              20

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 5:

CCATCAAGGC TCTGTATCCA TTC                                                          23

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 6:

ATAAAGTCT TCATGTTGGC ACTC                                                          24

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 7:

ACAGGTTCAC AGTTTTTCTC TTGAAG                                                       26

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 8:

GTAGGTCCGC TAGCAGTAC                                                               19

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 9:

AGAAGCAGTC TTCATACACG CGG                                                          23

(2) INFORMATION FOR SEQ ID NO: 10:

(i) SEQUENCE CHARACTERISTICS:
        (A) LENGTH: 18 base pairs
        (B) TYPE: nucleic acid ( C ) STRANDEDNESS: single
( D ) TOPOLOGY: linear ( x i ) SEQUENCE DESCRIPTION: SEQ ID NO: 10:

```
ACTGCTCATC GGCTGTTG                                                              18
```

( 2 ) INFORMATION FOR SEQ ID NO: 11:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 11:

```
TCAGCCATGT CCAGGTG                                                               17
```

( 2 ) INFORMATION FOR SEQ ID NO: 12:

( i ) SEQUENCE CHARACTERISTICS:
( A ) LENGTH: 4129 base pairs
( B ) TYPE: nucleic acid
( C ) STRANDEDNESS: double
( D ) TOPOLOGY: linear ( i x ) FEATURE:
( D ) OTHER INFORMATION: The sequence is preceded by an
unsequenced portion of from 4.7 to 5.3
kilobases ( x i ) SEQUENCE DESCRIPTION: SEQ ID NO: 12:

```
GAGTGCAGTG GTATGATCTG GGCTCACTGC AAGCTCTGCC TCCTGGGTTC ATGCCATTCT      60
CCTGACTCAG CCTCCCAAGT AGCTGGGACT ACAGGTGCCC GCTACCATGC CTGGCTAATT     120
TTTTGTATTT ATAGTAGAGA TGTCATTTCA CTGTGTTAGC CAGGATGGTC TCAATCTCCT     180
GACCTCGTGA TCCACACGCC TTGACCTCCC AAAGTGCTGC GATTACAGGT GTGAGCCACC     240
GTGCCCGGCC TTATACTTCT TTTTACTTT  TTTTCAGTGG TTTCCCTAGA GTTTGCAACA     300
TACATTTACA ACTAATTCAA ATCCACTTTC AAATAACACT ATACCATTTC ATAGGCATTA     360
TGAGTATCTT AAAATAATCC TAATTCCTTC CTCCTGTAAA CTAAAACAA  AATCCTAAAT     420
CCTCCAAACA ACTGAATGGA CCCCCTCTTC ACCAAGGGGA CCCCAGGGAA ACCTGAAAAA     480
CTGAGTGTTG GCCATGACGG GAAGGGAGGT GAGAGATGCT CATTATACTC CCTCCCTTTT     540
AGAGTTTTAG GTACAACTGA CCAGCATTAA TTTTAAAATA GAGATTACAG GACTGACAGA     600
ATGAACTCTT TGTGGCAATA TCAAATTAGG AACAAGACAA TGCAAGGAAA GGGTTAAATC     660
ATGCCCTTCA AACCATAAAA AAATTTTTT  TTAATTAACC CCATATAATG TGGTATACTT     720
TCCAAACTGA CTCTGGTATA GCATCACATG ACAGATTGCA GACTCCCTTA CCTTAAGCAT     780
TCCTTTATAC TGACTTCAAG TCTTAAGACA GAGCTGAACT CTTTCAACCA GCTGCTAACT     840
AAAGAATACC TAAAACCCAC CTGTGACTTG TAAGTCTCTG CTTTGCCATG TCCTGCCTTT     900
TCAGGCTGAC CCAATGTATA CCTTCCGTGT ATTGATTTAT GATTTTACC  TACAATTCCT     960
GTCTTCCTGA AACATATAAA ACCAAATCAT AACCCAACCA CCTCAGGCAC ACTTTCTCAG    1020
GACCTCTTGA GACTATTCTC CCGGCCATGG TCATTCATAT CGGCACAGAA TGAAACCTCT    1080
TTAAAATATT TTGCAGTTTT TTTCTTTCTG TTAACATTCC TTTCCCTTGT ATCATTGCTG    1140
TTATTAATTT CAAGTATATA TAAGCATACC TAATTAAATA CATTGTTGCT ATTATTCATT    1200
TTTGAACAAA CTATTATCTG TTAAATCAAC TAAGAATAAG ACAAATATGT TGGGTGCAGT    1260
GGTGCATGCC TATAGTCTCA GCTACTCAGA GGCTGAGGCA GGAGGATTGC TTGAGCTCAG    1320
```

| | | | | | | |
|---|---|---|---|---|---|---|
| GAGTTTAAGA | CCAGCCTAGG | CAACTTAGCA | AGATCATGTC | TCTTAAAAAA | AAAAAAGAA | 1380 |
| AGAAAGAAAA | ACAAAGTTTT | AGGAGGCTGA | GGCAGGAGTA | TCACTTGAAC | CCAGGACGCA | 1440 |
| GAGGTTGCAG | TGAGCCGAGA | TCGTGCCATT | ATACTCCAGC | CTGGGCAACA | GAGTGAGACT | 1500 |
| CTGTCTCAAA | AAAAAAAAG | AAAAGAAAAG | AAAAGAAAAA | AAAAGTTTTT | ATTTTACCTT | 1560 |
| CACTTATTCC | TTCTTGGATG | TTCTTCCTTT | ATGTAGGTAC | AAGGTTCTGA | CCTATGTTAT | 1620 |
| TTTCTTTTTC | TCTAAAGAAC | TTCAAAAGTT | TCCTGCAAGG | CAGGTCTACT | GGCAATGAAT | 1680 |
| TCCCTCAATT | TTTGCTTGAC | AAAGTCTTTA | TTTCTGCTTC | ACTATTGATG | GATAATTTCA | 1740 |
| CAAGAGTGTT | CCTTTTGTAG | ATTCACTCTT | CTTATCCTTC | CCTTCAGAAA | TATTCTTTGA | 1800 |
| CCAACTATTG | GGTCCCAGGT | ACTGCACTAG | AGCTTTACTT | CTAGTTAATT | CCCACAGCAA | 1860 |
| TTCTGAGAGG | TAGGTAGGTA | TTATATTCCT | AGATGCAAAC | TCAGAATTCA | GAAGGTAAAG | 1920 |
| TGATGAGACT | GAAGGCACAC | AGCAAGTAAG | TGGCAGAACC | TAGATTAAAA | CTCATTCTTA | 1980 |
| AAACTTTGGC | TTCCTTCTCT | TTTCTTTAAT | GGATTCAGTT | ACTTCTTCTC | ACCCACTCAC | 2040 |
| CTTTATCAAT | TTACATTTCA | GATAAAGTC | TTCATGTTGG | CANCTCAATG | TGCCTTAACA | 2100 |
| AGAAGATGCC | CACAAGAAGG | GTTTGATCAT | CGGGACAGCA | AAGTGTCTCT | TCAAGAGAAA | 2160 |
| AACTGTGAAC | CTGTGGTAGG | TTAAGATCCT | TCATAAGGGT | ATTTTCATGA | ATGGCTGTTT | 2220 |
| TTAACTCAAG | TGAATACAAT | TATTTCCATT | TAAAAAGCAA | GGACAATGTG | AATGTACTCA | 2280 |
| TTGCCACTGA | ACTATATACA | CCTAAAAATG | GTTAAAATGG | CAACTTTTAT | GTGTATTTTA | 2340 |
| TGAGAATAAA | AAATAAATAA | TAATAAAAAA | CAAGGGAAGT | ACAGATATTT | TCTTAATTGT | 2400 |
| GTTGTCACAT | ACCCAGTGTT | TCCAGGGTCA | ATAATGAGAG | CCCTACATGT | AAGATTCAAA | 2460 |
| GGAAGAATTT | AGTCCTGGAT | ACAATATTCT | TTTATGTTTT | TAGTTATATT | TGCCTTTTTA | 2520 |
| ATGGATGCAG | ATATATACAG | AGGGAAGGGA | TAAAGTACCT | ATTATTTATT | GTATAGAGCT | 2580 |
| GTGCTGTCTG | ATGGCTTAGC | CACTAGTCAC | ATGGTGCTAT | TGAACACTTA | AAACACAGGA | 2640 |
| GTTTGAAATA | AGCATGTATT | ATAATACATA | TCATATTTCA | AAAATATTAG | TATGTAGAAA | 2700 |
| AGAAGATAAA | TGGTTCATTA | ATGATTTTA | TATTGATTCA | CCTTGAAATA | AATATTCTGA | 2760 |
| AAATATTAGG | TTAAACAAAA | TATTTTAAGA | TTAATTTTAC | ATGTTTCTTC | TTTTAAATGT | 2820 |
| AGCTACTAGA | AATTTTAAAA | TTACATATGG | CTGGGCATGG | TGGCTCACAC | CTGTAATCCC | 2880 |
| AGCACTTCGG | GAGGCCGAGG | TGGGTGGATC | ACCTGATCTC | AGGAGCTCGA | GACCAGCCTG | 2940 |
| GCAAACATGG | TGAAATCCTA | TCTTTACTAA | AAATACAAAA | ATTAGCCAAG | CGTGGTGGTG | 3000 |
| CATGCCTGTA | ATCCCAGCTA | CTTGGGACGC | TGAGGCAGGA | GAATCACTTG | AACCCGGGAG | 3060 |
| GTGGAGGTTG | CAGTGAGCCG | AGATAGTGCC | ACTGCACTCC | AGCCTGGGAG | ACAAGAGCAA | 3120 |
| AACTCCATCT | CAAAAATAAA | TAAATAAAAT | AAAATTACAT | AAGTGGCTTG | TACCATATTT | 3180 |
| CTATTGGACA | GCACTAGTAC | ATATACAACA | CAGCATAATG | GTTGAGAGCA | CTGACTCTGG | 3240 |
| AGCCAAATTA | CTGTGTTTGA | TTCTTAGCTC | CACAACTTAC | TAGTTGTGTG | ACCATGGGCA | 3300 |
| AGCGAGTTAA | CCTCTCTGTG | CCCCAGTTTC | CCATTCTGTA | ACATGAAAAT | AATAAAAACA | 3360 |
| CTCCCCAGAA | TTGTTGTGAG | CATTAAATGA | AGCCCTGACA | CATTTGTTCT | GGATACAATA | 3420 |
| TCCTCTTGTT | TTATATTTGG | TAGTATCAAT | GTGCCTTTAG | ACACAATTAC | AACGATCTCT | 3480 |
| GTGGTAAAGA | TGCAATGTAT | ATGGTGTCTA | TAAATAGCAT | TCAATGATTC | GTTAGTTAGG | 3540 |
| GCTTGAGACT | TTTACTGTCA | TGGAAAATCT | AGGTATAGCT | AAGCTTTTGA | GATTTTGGGA | 3600 |
| ACTCCTTAAC | CCTATTTTTC | TCTACTCTTG | CCCCCAACAA | TCAGCCTATA | TACTTGTGAA | 3660 |
| ATTTAACAAT | TACTTCACTG | GGCAGAAATT | ATATGGGAAC | ACTTAGAAAT | TTCAGTCCAC | 3720 |

| | | | | | | |
|---|---|---|---|---|---|---|
| AGGGAAAGTA | TAAATATGTT | AACTATTTTA | ACTTAATCCC | TTCCTAGAAA | CACATACACT | 3780 |
| GTTGCCAAGC | CCATATTCTC | CCTTTCTTGT | TCTCACAGTT | CCCAATGCTC | CACCTGCTTA | 3840 |
| TGAGAAACTC | TCTGCAGAAC | AGTCACCACC | ACCTTATTCA | CCTTAAGAGC | CAGCGAGACA | 3900 |
| CCTGAGACAT | GCTGAAATTA | TTTCTCTCAC | ACTTTTGCTT | GAATTTAATA | CAGACATCTA | 3960 |
| ATGTTCTCCT | TTGGAATGGT | GTAGGAAAAA | TGCAAGCCAT | CTCTAATAAT | AAGTCAGTGT | 4020 |
| TAAAATTTTA | GTAGGTCCGC | TAGCAGTACT | AATCATGTGA | GGAAATGATG | AGAAATATTA | 4080 |
| AATTGGGAAA | ACTCCATCAA | TAAATGTTGC | AATGCATGAT | AAAAAAAA | | 4129 |